(12) United States Patent
Conley et al.

(10) Patent No.: US 7,761,161 B2
(45) Date of Patent: *Jul. 20, 2010

(54) CARDIAC RHYTHM MANAGEMENT SYSTEM WITH USER INTERFACE FOR THRESHOLD TEST

(75) Inventors: Vickie L. Conley, Woodbury, MN (US); Allan T. Koshiol, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 701 days.

This patent is subject to a terminal disclaimer.

(21) Appl. No.: 11/427,404

(22) Filed: Jun. 29, 2006

(65) Prior Publication Data

US 2006/0241714 A1    Oct. 26, 2006

Related U.S. Application Data

(63) Continuation of application No. 10/692,295, filed on Oct. 23, 2003, now Pat. No. 7,096,065, which is a continuation of application No. 10/021,861, filed on Dec. 17, 2001, now Pat. No. 6,671,551, which is a continuation of application No. 09/378,106, filed on Aug. 20, 1999, now Pat. No. 6,353,761.

(51) Int. Cl.
*A61N 1/362* (2006.01)

(52) U.S. Cl. ...................................... 607/27
(58) Field of Classification Search ............. None
See application file for complete search history.

(56) References Cited

U.S. PATENT DOCUMENTS

| | | | | |
|---|---|---|---|---|
| 4,705,043 A | * | 11/1987 | Imran | 607/4 |
| 5,458,623 A | | 10/1995 | Lu et al. | |
| 5,578,063 A | * | 11/1996 | Bocek et al. | 607/5 |
| 5,601,615 A | * | 2/1997 | Markowitz et al. | 607/28 |
| 5,683,427 A | | 11/1997 | Ekwall | |
| 5,683,431 A | | 11/1997 | Wang | |
| 5,713,933 A | | 2/1998 | Condie et al. | |

(Continued)

FOREIGN PATENT DOCUMENTS

EP    0310216 A2    4/1989

OTHER PUBLICATIONS

"Medtronic.Sigma™ 300/200/100 Series Pacemaker Programming Guide", Introduction, Table of Contents and Chapter 5, (1999) 44 pgs.

*Primary Examiner*—Carl H. Layno
*Assistant Examiner*—Jon-Eric C. Morales
(74) *Attorney, Agent, or Firm*—Schwegman, Lundberg & Woessner, P.A.

(57) ABSTRACT

An implantable cardiac rhythm management system includes a user interface, such as an external programmer, for performing therapy energy threshold tests. The threshold tests allow the caregiver to determine the threshold energy at which paces capture the heart, i.e., cause a resulting contraction of the heart chamber to which the paces are delivered. The programmer provides recorded indications of the energy corresponding to each paced event, so that the caregiver can easily determine the point at which capture was lost. This recorded representation of pacing energy makes it easy for the caregiver to determine proper pacing thresholds to be used to ensure adequate pacing, while minimizing energy drain to prolong the useful life of the implanted device.

20 Claims, 6 Drawing Sheets

U.S. PATENT DOCUMENTS

| | | |
|---|---|---|
| 5,722,999 A | 3/1998 | Snell |
| 5,724,985 A | 3/1998 | Snell et al. |
| 5,749,908 A | 5/1998 | Snell |
| 5,800,466 A | 9/1998 | Routh et al. |
| 5,861,012 A * | 1/1999 | Stroebel .................. 607/28 |
| 5,908,392 A | 6/1999 | Wilson et al. |
| 5,954,755 A | 9/1999 | Casavant |
| 5,974,341 A | 10/1999 | Er et al. |
| 6,016,442 A | 1/2000 | Hsu et al. |
| 6,035,233 A | 3/2000 | Schroeppel et al. |
| 6,038,476 A | 3/2000 | Schwartz |
| 6,091,990 A | 7/2000 | Hsu et al. |
| 6,101,415 A * | 8/2000 | Er et al. ..................... 607/27 |
| 6,216,036 B1 | 4/2001 | Jenkins et al. |
| 6,243,606 B1 | 6/2001 | Mann et al. |
| 6,246,912 B1 * | 6/2001 | Sluijter et al. ............. 607/100 |
| 6,353,761 B1 * | 3/2002 | Conley et al. ............. 607/28 |
| 6,671,551 B2 | 12/2003 | Conley et al. |
| 7,096,065 B2 * | 8/2006 | Conley et al. ............. 607/27 |
| 2002/0045804 A1 * | 4/2002 | Christopherson et al. ... 600/300 |
| 2002/0095190 A1 | 7/2002 | Bornzin et al. |

* cited by examiner

CARDIAC RHYTHM MANAGEMENT SYSTEM WITH USER INTERFACE FOR THRESHOLD TEST

CROSS-REFERENCE TO RELATED APPLICATION(S)

This application is a continuation of U.S. patent application Ser. No. 10/692,295, filed on Oct. 23, 2003, now issued as U.S. Pat. No. 7,096,065, which is a continuation of U.S. patent application Ser. No. 10/021,861, filed on Dec. 17, 2001, now issued as U.S. Pat. No. 6,671,551, which is a continuation of U.S. patent application Ser. No. 09/378,106, filed on Aug. 20, 1999, now issued as U.S. Pat. No. 6,353,761, the specifications of which are hereby incorporated by reference.

TECHNICAL FIELD

The present system relates generally to cardiac rhythm management systems and particularly, but not by way of limitation, to a cardiac rhythm management system providing, among other things, a user interface for threshold testing.

BACKGROUND

When functioning properly, the human heart maintains its own intrinsic rhythm, and is capable of pumping adequate blood throughout the body's circulatory system. However, some people have irregular cardiac rhythms, referred to as cardiac arrhythmias. Such arrhythmias result in diminished blood circulation. One mode of treating cardiac arrhythmias uses drug therapy. Anti-arrhythmic drugs are often effective at restoring normal heart rhythms. However, drug therapy is not always effective for treating arrhythmias of certain patients. For such patients, an alternative mode of treatment is needed. One such alternative mode of treatment includes the use of a cardiac rhythm management system. Such systems often include portions that are implanted in the patient and deliver therapy to the heart.

Cardiac rhythm management systems include, among other things, pacemakers, also referred to as pacers. Pacers deliver timed sequences of low energy electrical stimuli, called pace pulses, to the heart, such as via an intravascular leadwire or catheter (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly.

Cardiac rhythm management systems also include cardioverters or defibrillators that are capable of delivering higher energy electrical stimuli to the heart. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering a high energy electrical stimulus that is sometimes referred to as a defibrillation countershock. The countershock interrupts the tachyarrhythmia, allowing the heart to reestablish a normal rhythm for the efficient pumping of blood. In addition to pacers, cardiac rhythm management systems also include, among other things, pacer/defibrillators that combine the functions of pacers and defibrillators, and any other implantable or external systems or devices for diagnosing or treating cardiac arrhythmias.

One problem faced by cardiac rhythm management systems is determining whether the therapy delivered has had its desired effect. For example, after implanting a pacer in a patient, a physician or other caregiver would like to know if the pace pulses being delivered are effective at "capturing the heart," i.e., evoking a contraction of the heart chamber to which the pace pulse was delivered. If the paces are not succeeding at capturing the heart, the physician will likely program a higher energy pace pulse to obtain capture. In order to save energy, prolonging the useful life of the implanted device before replacement is required, lower energy paces are preferable provided that the physician is assured that the lower energy pace pulses will capture the heart. Replacement of the implanted device carries significant expense as well as some risk of discomfort and/or complications.

In order to determine the appropriate energy of pacing therapy, the physician typically programs several different therapy energy levels (i.e., pacing voltage amplitude, pacing pulsewidth, or combination of amplitude and pulsewidth) to see what energy levels appropriately obtain capture. Because proper therapy energy levels are critical in providing effective cardiac rhythm management therapy and extending the useful life of the implanted device, there is a need for techniques that assist the physician or other caregiver in determining threshold energies for cardiac rhythm management therapy.

SUMMARY OF THE INVENTION

This document describes, among other things, portions of cardiac rhythm management system including a user interface for performing therapy energy threshold tests. In one embodiment, the user interface includes a programmer that provides recorded indications of the energy corresponding to paced events, so that the caregiver can easily determine the point at which capture was lost. This recorded representation of pacing energy makes it easy for the caregiver to determine proper pacing thresholds to be used to ensure adequate pacing, while minimizing energy drain to prolong the useful life of the implanted device.

In one embodiment, the cardiac rhythm management system includes an external user interface. The user interface includes a communication module, adapted for remote communicative coupling to the implantable device. The user interface also includes a threshold testing module. The user interface provides a recorded output indicator of energy associated with an instance of therapy delivery by the implantable device.

This document also describes a method that includes pacing a patient at varying energies and recording a separate output indicator of energy associated with each pace. These and other aspects of the present system and methods will become apparent upon reading the following detailed description and viewing the accompanying drawings that form a part thereof.

BRIEF DESCRIPTION OF THE DRAWINGS

In the drawings, like numerals describe substantially similar components throughout the several views. Like numerals having different letter suffixes represent different instances of substantially similar components.

DETAILED DESCRIPTION

Figure 1:
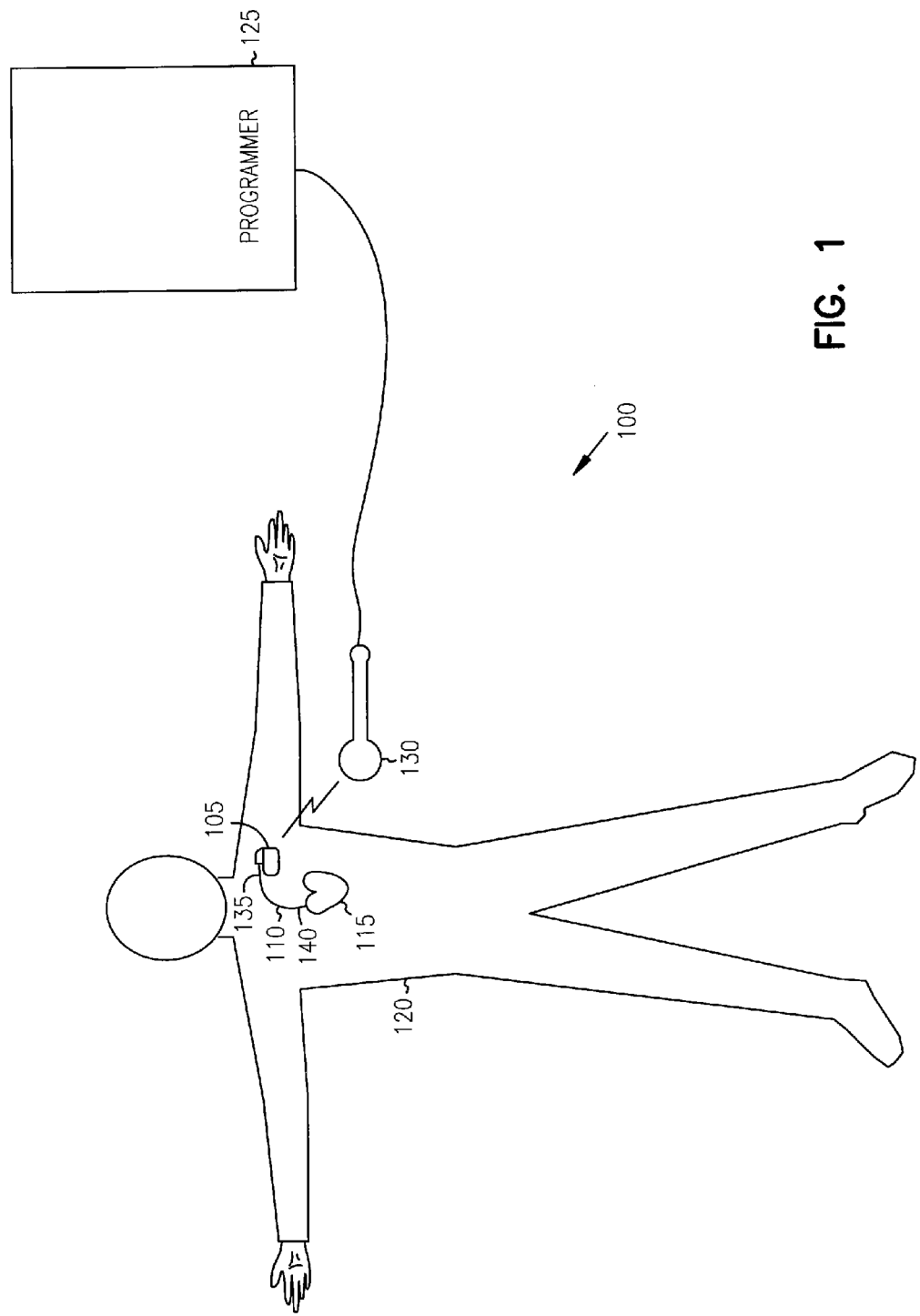
FIG. 1 is a schematic drawing illustrating generally one embodiment of portions of a cardiac rhythm management system and an environment in which it is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents. In the drawings, like numerals describe substantially similar components throughout the several views. Like numerals having different letter suffixes represent different instances of substantially similar components. In this document, "and/or" refers to non-exclusive "or" (e.g., "A and/or B" includes each of "A but not B." "B but not A," and "A and B").

The present methods and apparatus will be described in applications involving implantable medical devices including, but not limited to, implantable cardiac rhythm management systems such as pacemakers, cardioverter/defibrillators, pacer/defibrillators, and biventricular or other multi-site coordination devices. However, it is understood that the present methods and apparatus may be employed in unimplanted devices, including, but not limited to, external pacemakers, cardioverter/defibrillators, pacer/defibrillators, biventricular or other multi-site coordination devices, monitors, programmers and recorders.

General System Overview and Examples

This document describes, among other things, a cardiac rhythm management system with a user interface for a threshold test. FIG. 1 is a schematic drawing illustrating generally, by way of example, but not by way of limitation, one embodiment of portions of a cardiac rhythm management system 100 and an environment in which it is used. In FIG. 1, system 100 includes an implantable cardiac rhythm management device 105, also referred to as an electronics unit, which is coupled by an intravascular endocardial lead 110, or other lead, to a heart 115 of patient 120. System 100 also includes an external user interface, such as programmer 125, providing wireless communication with device 105 using a communication module such as telemetry device 130. Catheter lead 110 includes a proximal end 135, which is coupled to device 105, and a distal end 140, which is coupled to one or more portions of heart 115.

Figure 2:
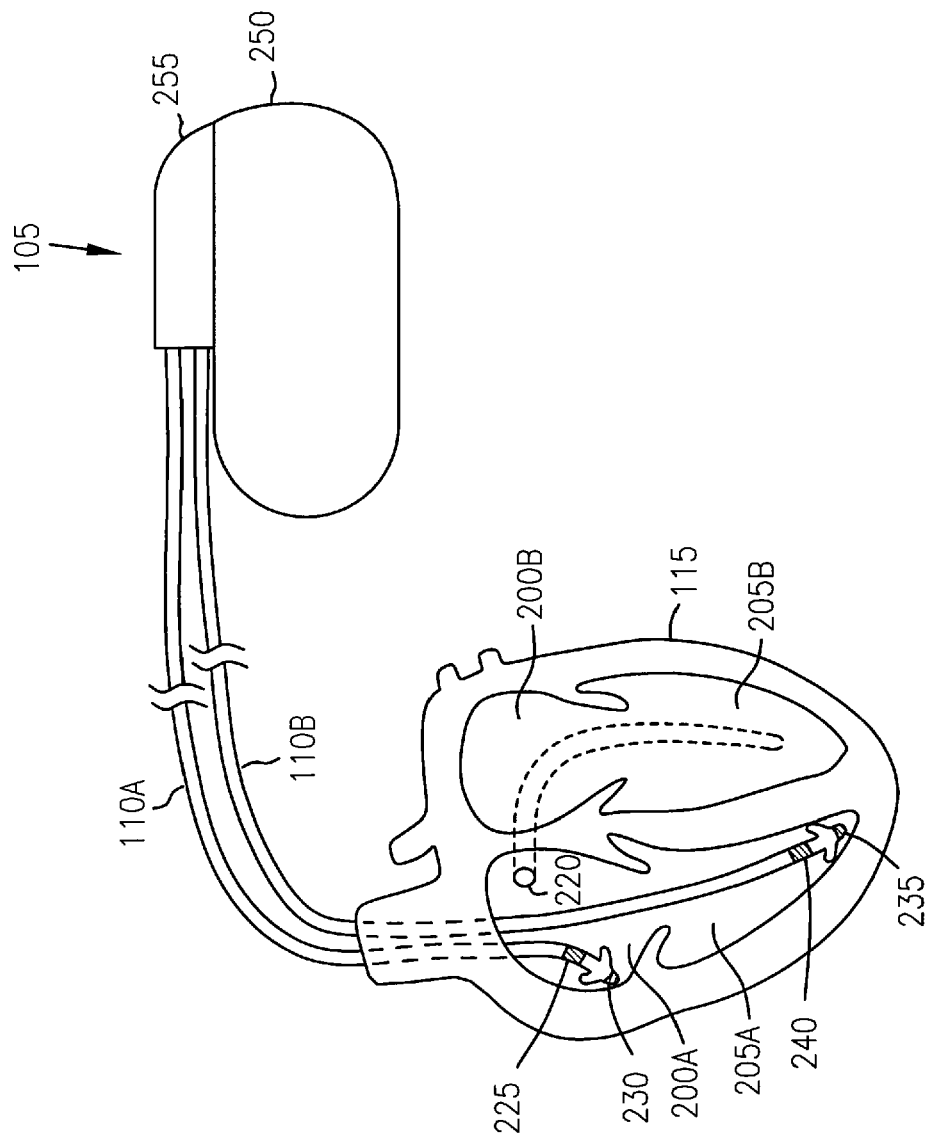
FIG. 2 is a schematic drawing illustrating generally one embodiment of a cardiac rhythm management device coupled by leads to a heart.

FIG. 2 is a schematic drawing illustrating generally, by way of example, but not by way of limitation, one embodiment of device 105 coupled by leads 110A-B to heart 115, which includes a right atrium 200A, a left atrium 200B, a right ventricle 205A, a left ventricle 205B, and a coronary sinus 220 extending from right atrium 200A. In this embodiment, atrial lead 110A includes electrodes (electrical contacts) disposed in, around, or near an atrium 200 of heart 115, such as ring electrode 225 and tip electrode 230, for sensing signals and/or delivering pacing therapy to the atrium 200. Lead 110A optionally also includes additional electrodes, such as for delivering atrial and/or ventricular cardioversion/defibrillation and/or pacing therapy to heart 115.

In FIG. 2, a ventricular lead 110B includes one or more electrodes, such as tip electrode 235 and ring electrode 240, for delivering sensing signals and/or delivering pacing therapy. Lead 110B optionally also includes additional electrodes, such as for delivering atrial and/or ventricular cardioversion/defibrillation and/or pacing therapy to heart 115. Device 105 includes components that are enclosed in a hermetically-sealed can 250. Additional electrodes may be located on the can 250, or on an insulating header 255, or on other portions of device 105, for providing unipolar pacing and/or defibrillation energy in conjunction with the electrodes disposed on or around heart 115. Other forms of electrodes include meshes and patches which may be applied to portions of heart 115 or which may be implanted in other areas of the body to help "steer" electrical currents produced by device 105. In one embodiment, one of atrial lead 110A or ventricular lead 110B is omitted, i.e., a "single chamber" device is provided, rather than the dual chamber device illustrated in FIG. 2. In another embodiment, additional leads are provided for coupling device 105 to other heart chambers and/or other locations in the same heart chamber as one or more of leads 110A-B. The present method and apparatus will work in a variety of configurations and with a variety of electrical contacts or "electrodes."

Example Cardiac Rhythm Management Device

Figure 3:
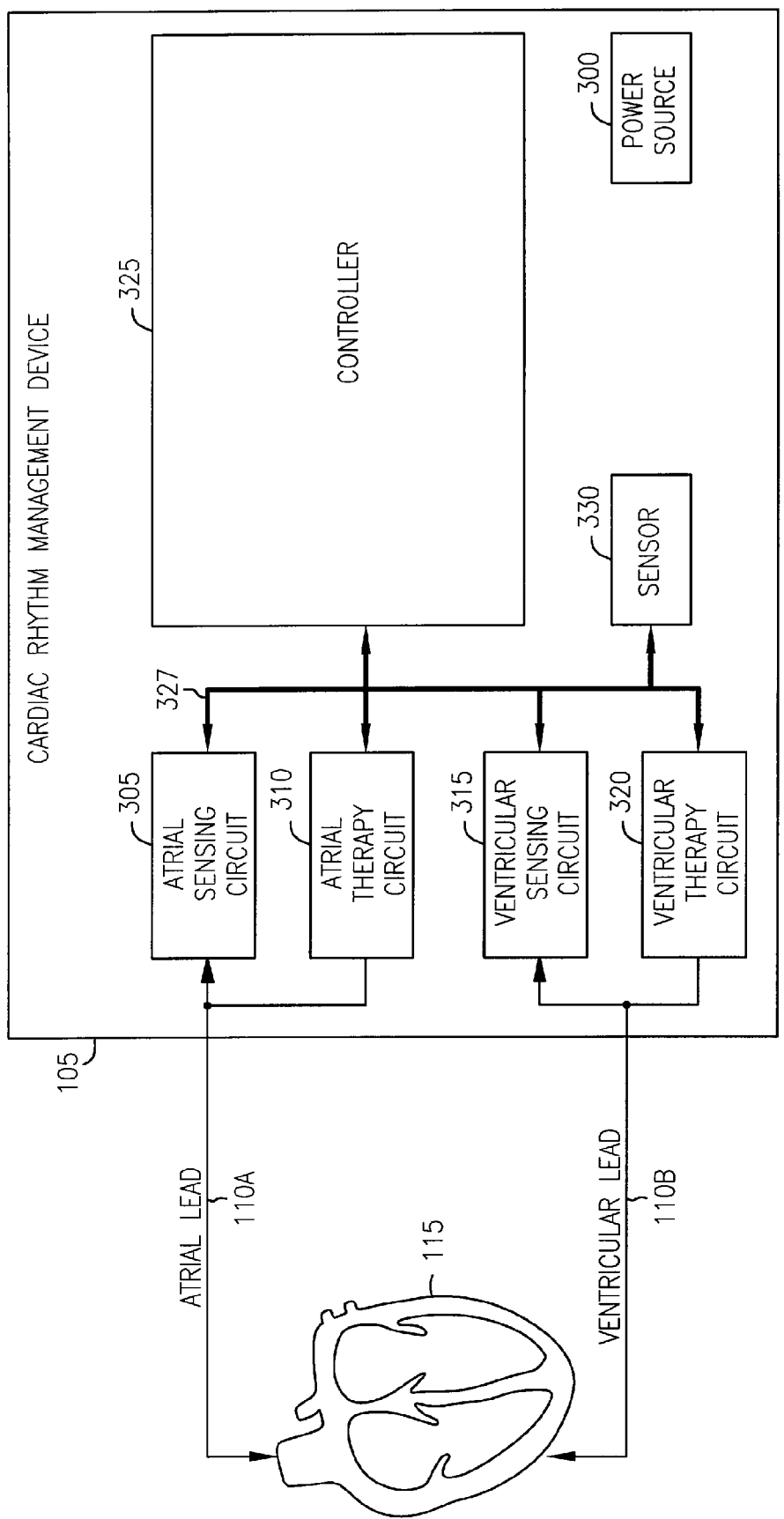
FIG. 3 is a schematic diagram illustrating generally one embodiment of portions of a cardiac rhythm management device coupled to heart.

FIG. 3 is a schematic diagram illustrating generally, by way of example, but not by way of limitation, one embodiment of portions of device 105, which is coupled to heart 115. Device 105 includes a power source 300, an atrial sensing circuit 305, an atrial therapy circuit 310, a ventricular sensing circuit 315, a ventricular therapy circuit 320, and a controller 325.

Atrial sensing circuit 305 is coupled by atrial lead 110A to heart 115 for receiving, sensing, and/or detecting electrical atrial heart signals. Such atrial heart signals include atrial activations (also referred to as atrial depolarizations or P-waves), which correspond to atrial contractions. Such atrial heart signals include normal atrial rhythms, and abnormal atrial rhythms including atrial tachyarrhythmias, such as atrial fibrillation, and other atrial activity. Atrial sensing circuit 305 provides one or more signals to controller 325, via node/bus 327, based on the received atrial heart signals.

In one embodiment, atrial therapy circuit 310 provides atrial pacing therapy, as appropriate, to electrodes located at or near one of the atria 200 of heart 115 for obtaining resulting evoked atrial depolarizations. In a further embodiment, atrial therapy circuit 310 also provides cardioversion/defibrillation therapy, as appropriate, to electrodes located at or near one of the atria 200 of heart 115, for terminating atrial fibrillation and/or other atrial tachyarrhythmias.

Ventricular sensing circuit 315 is coupled by ventricular lead 110B to heart 115 for receiving, sensing, and/or detecting electrical ventricular heart signals, such as ventricular activations (also referred to as ventricular depolarizations or R-waves), which correspond to ventricular contractions. Such ventricular heart signals include normal ventricular rhythms, and abnormal ventricular rhythms, including ventricular tachyarrhythmias, such as ventricular fibrillation, and other ventricular activity. Ventricular sensing circuit 315 provides one or more signals to controller 325, via node/bus 327, based on the received ventricular heart signals.

In one embodiment, ventricular therapy circuit 320 provides ventricular pacing therapy, as appropriate, to electrodes located at or near one of the ventricles 205 of heart 115 for obtaining resulting evoked ventricular depolarizations. In a further embodiment, ventricular therapy circuit 320 also provides cardioversion/defibrillation therapy, as appropriate, to electrodes located at or near one of the ventricles 205 of heart 115, for terminating ventricular fibrillation and/or other ventricular tachyarrhythmias.

Controller 325 controls the delivery of therapy by atrial therapy circuit and/or ventricular therapy circuit 320 and/or other circuits, based on heart activity signals received from atrial sensing circuit 305 and ventricular sensing circuit 315, as discussed below. Controller 325 includes various modules, which are implemented either in hardware or as one or more sequences of steps carried out on a microprocessor or other controller. Such modules are illustrated separately for conceptual clarity; it is understood that the various modules of controller 325 need not be separately embodied, but may be combined and/or otherwise implemented, such as in software/firmware.

In general terms, sensing circuits 305 and 315 sense electrical signals from heart tissue in contact with the catheter leads 110A-B to which these sensing circuits 305 and 315 are coupled. Sensing circuits 305 and 315 and/or controller 325 process these sensed signals. Based on these sensed signals, controller 325 issues control signals to therapy circuits, such as ventricular therapy circuit 320, if necessary, for the delivery of electrical energy (e.g., pacing and/or defibrillation pulses) to the appropriate electrodes of leads 110A-B. Controller 325 may include a microprocessor or other controller for execution of software and/or firmware instructions. The software of controller 325 may be modified (e.g., by remote external programmer 125) to provide different parameters, modes, and/or functions for the implantable device 105 or to adapt or improve performance of device 105.

In one further embodiment, one or more sensors, such as sensor 330, may serve as inputs to controller 325 for adjusting the rate at which pacing or other therapy is delivered to heart 115. One such sensor 330 includes an accelerometer that provides an input to controller 325 indicating increases and decreases in physical activity, for which controller 325 increases and decreases pacing rate, respectively. Another such sensor includes an impedance measurement, obtained from body electrodes, which provides an indication of increases and decreases in the patient's respiration, for example, for which controller 325 increases and decreases pacing rate, respectively. Any other sensor 330 providing an indicated pacing rate can be used.

Example Threshold Test

Device 105 includes, among other things, a pacing threshold test module included in software and/or hardware of controller 325. Using an icon on the screen display of external programmer 125, the physician or other caregiver initiates a pacing threshold test mode that allows observation of the effectiveness of varying therapy energy levels at capturing the heart, i.e., at obtaining a resulting contraction of the heart chamber to which the energy is delivered. Energy levels are varied by changing either the amplitude or the pulsewidth of the delivered pacing pulse. During the threshold test, data is communicated from the implanted device 105 to the external user interface, e.g., programmer 125, using real-time telemetry by device 105 in response to synchronization pulses provided by programmer 125.

In one embodiment, amplitude is varied by changing the pacing amplitude to 5.0V for four paces, then stepping the energy down by 0.5V increments for each successive four paces down to a pacing amplitude of 3.0V. After that, the pacing amplitude continues to decrease by 0.2V increments, for each successive four paces, until the pacing amplitude reaches 0.2V. As the pacing amplitudes are decreased, the caregiver observes on the screen display of programmer 125 a corresponding electrogram signal, i.e., a cardiac signal associated with the particular chamber of the heart to which the pace pulses are delivered. If the caregiver notices that the pacing pulses being delivered fail to capture the heart (i.e., the characteristic depolarization is absent after the pace pulse is delivered), the caregiver ends the threshold test, such as by using an icon on the user interface. When the caregiver ends the threshold test, the user interface displays the last pacing amplitude delivered before capture was lost. The caregiver can then set the pacing amplitude to that value, or alternatively, the caregiver can add an appropriate "safety margin" when setting the pacing amplitude.

During the pacing threshold test, the previously programmed pacing parameters (amplitude, pulsewidth, rate, AV delay, etc.) are stored. In one embodiment, after the pacing threshold test is ended, pacing continues at either the previously stored pacing parameter values, or at default values that are regarded as safe enough to ensure capture (e.g., 5.0V amplitude, 0.5 millisecond pulsewidth). After a pacing threshold test is conducted for a particular chamber, the caregiver can retest pacing amplitudes. In one embodiment, a retest of pacing thresholds begins at the default initial values (e.g., amplitude of 5.0V or pulsewidth of 0.5 milliseconds). In another embodiment, however, a retest of pacing thresholds begins at a predetermined number of increments (e.g., 3 increments) above the energy level before which capture was lost. For example, if a first threshold test using amplitudes lost capture at 0.4V, as determined by the physician ending the threshold test, then, the screen display would indicate 0.6V as the threshold voltage before which capture was lost. In this example, a retest of pacing thresholds would begin at 1.2V, that is, at 3 increments of 0.2V above the previous minimum capture amplitude of 0.6V. By starting a retest of pacing thresholds at a predetermined number of increments above the result of the previous test, the time required for conducting a retest is reduced.

In one embodiment, the pacing amplitudes or pulsewidths are automatically stepped down (decremented) every fourth pace. In another embodiment, the pacing amplitudes or pulsewidths are manually decremented or incremented by the physician using the "+" and "−" icons on the screen display of programmer 125 and illustrated in FIG. 4.

Example Programmer Interface

Figure 4:
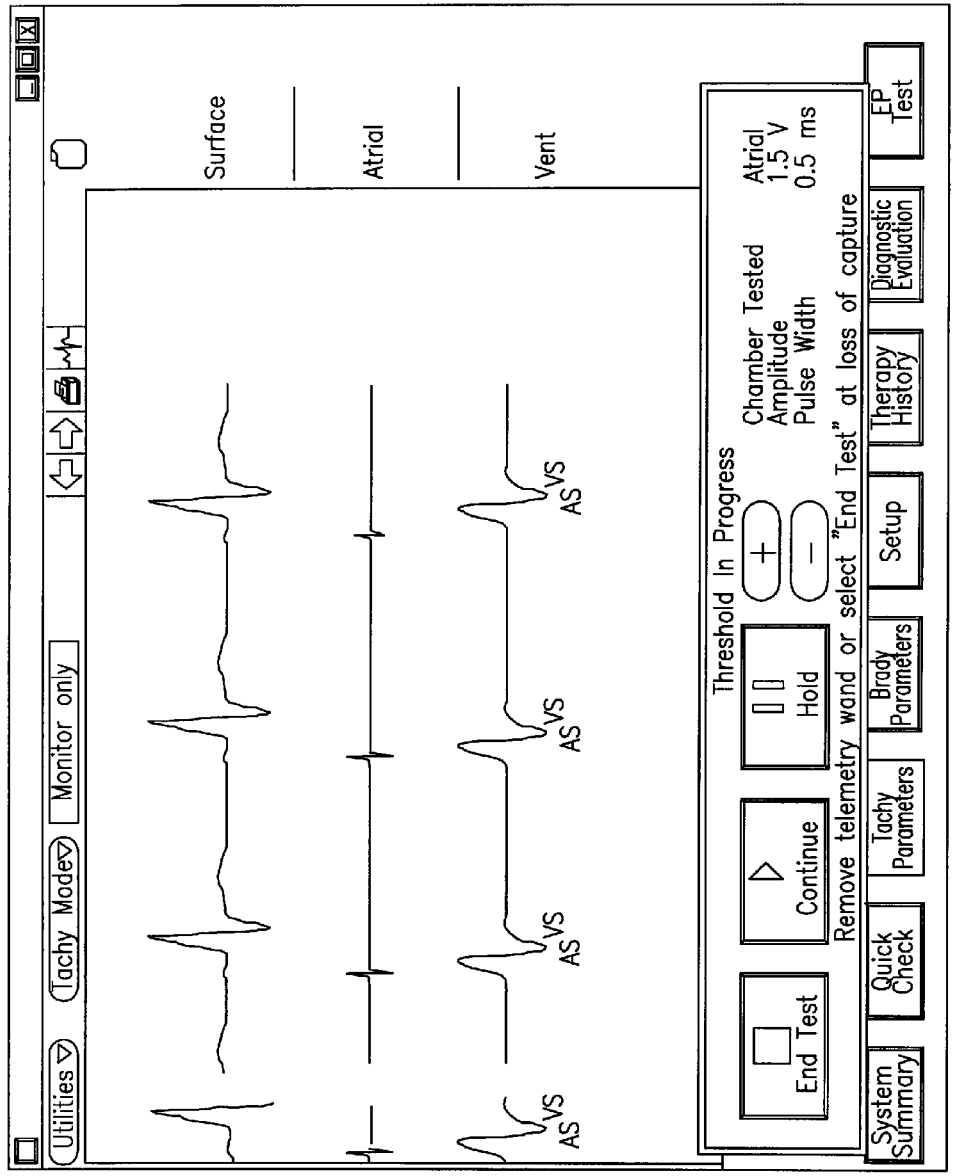
FIG. 4 illustrates generally one embodiment of a screen display associated with an external programmer or other user interface.

FIG. 4 illustrates generally, by way of example, but not by way of limitation, one embodiment of a screen display associated with external programmer 125. The screen display of FIG. 4 includes visual images of cardiac signals obtained from one or more implanted or external electrodes, such as surface electrodes and/or bipolar or unipolar atrial or ventricular implanted electrodes. The screen display also includes various icons, including an icon for starting/ending the threshold test. The threshold test is alternatively ended by removing the telemetry device 130 (e.g., wand) from near the implanted device 105 to interrupt communication therebetween. In threshold testing mode this screen display also includes information regarding the particular chamber being tested, the present amplitude of pace pulses being delivered (or the last pacing amplitude before loss of capture, after the threshold test is ended), and/or the present pacing pulsewidth.

The above-described threshold testing technique provides only one example of carrying out a threshold test to determine pacing thresholds. In an alternative embodiment, the pacing energy is varied by decreasing pacing pulsewidths (the duration of the pacing pulse) rather than by decreasing pacing amplitude. In another embodiment, either of amplitude or pulsewidth are increased, rather than decreased, until capture is obtained. Moreover, it is understood that the caregiver can select which electrodes are associated with a particular pacing threshold test, so that separate pacing thresholds are determined, for example, for atrial, ventricular, or other electrodes, or for unipolar or bipolar pacing configurations.

Returning to the above-described embodiment of decreasing pacing amplitudes to determine pacing threshold energies, it is apparent that the pacing threshold test is conducted "real time." The accuracy of the determined pacing threshold depends on the caregiver ending the threshold test when loss of capture is observed. However, other distractions, for example, may result in a less than adequate response time of the caregiver in ending the test. Moreover, proper medical recordkeeping may require that the physician records the test. For these and other reasons, programmer 125 includes a printer that provides a strip chart recording of the threshold test. Furthermore, programmer 125 also includes a screen display that also displays the information that is displayed by the recorded strip chart. In one embodiment, programmer 125 also includes a storage device (e.g., magnetic disk storage) that also stores the same data that is recorded on the strip chart.

Example Recorded Output

Figure 5:
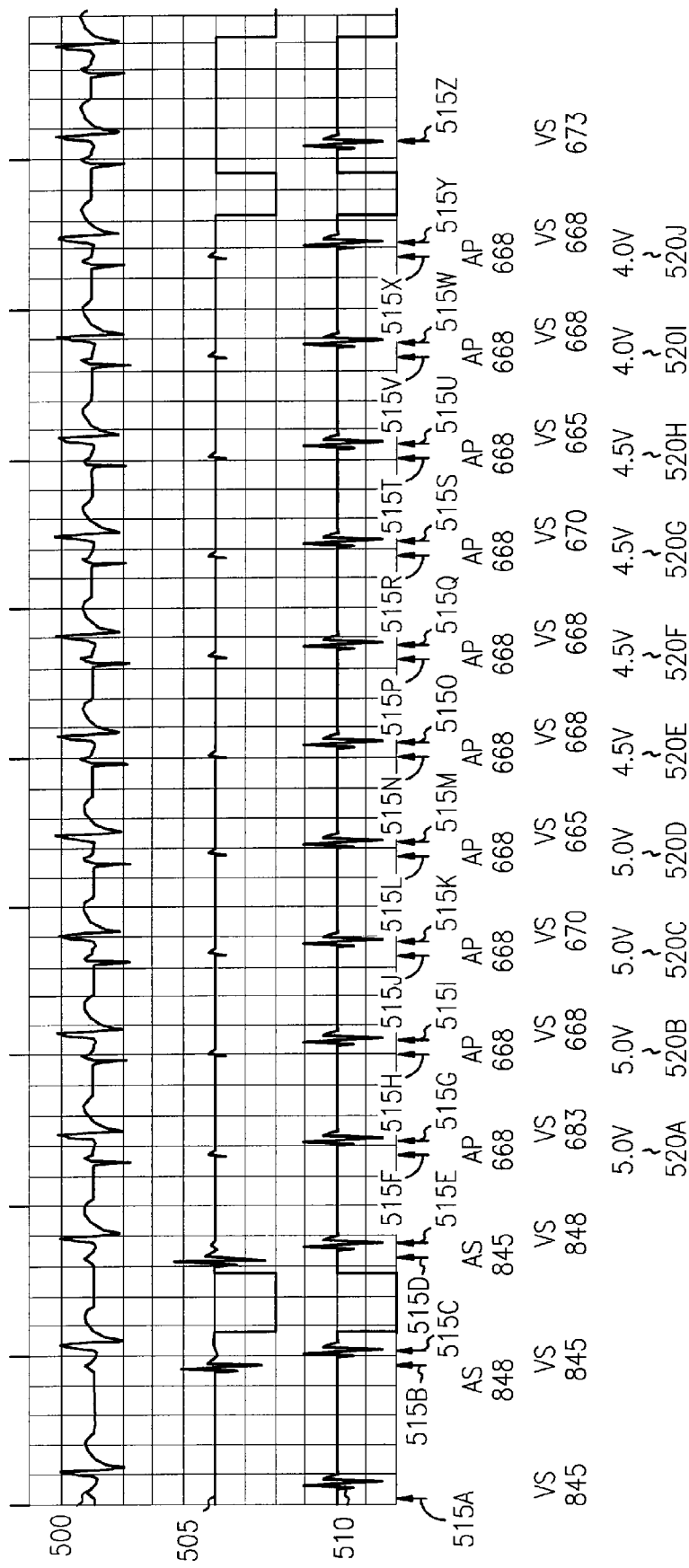
FIG. 5 is an example of a strip chart recording provided by a printer associated with a programmer.

FIG. 5 is an example of a strip chart recording provided by the printer associated with programmer 125. Based at least in part on data telemetered from implanted device 105 to external programmer 125, the strip chart recording provides real time electrograms of cardiac signals associated with one or more implanted or surface electrode sites. In the embodiment illustrated in FIG. 5, the strip chart includes cardiac signals from a surface electrogram 500, an atrial electrogram 505, and a ventricular electrogram 510. These signals include cardiac depolarizations that allow the caregiver to determine whether the particular heart chamber has contracted in response to a delivered pace of a particular energy.

The strip chart of FIG. 5 also includes atrial and ventricular event markers 515A-Z, indicated by upwardly pointing arrows. These arrows indicate the occurrence of a pace, delivered by atrial therapy circuit 310 or ventricular therapy circuit 320, or of a sensed cardiac depolarization, detected by atrial sensing circuit 305 or ventricular sensing circuit 315. Below corresponding event markers, the strip chart includes text describing information related to the particular event marker. "AS" indicates that the associated event marker corresponds to an atrial sense, "AP" indicates that the associated event marker corresponds to an atrial pace. Similarly, "VS" indicates that the associated event marker corresponds to a ventricular sense, "VP" indicates that the associated event marker corresponds to a ventricular pace. Other markers also exist. A corresponding numeral indicates the time interval in milliseconds since the previous event marker in the same chamber. The strip chart of FIG. 5 also includes output indicators 520A-J, based on data telemetered from the implanted device 105, of the energies associated with particular pace pulses. In FIG. 5, because atrial amplitude is being varied to determine atrial pacing thresholds, the output indicators of atrial amplitudes are printed below their corresponding event markers (e.g., output indicator 520A of 5.0V corresponds to atrial pace event marker 515F, output indicator 520B of 5.0V corresponds to atrial pace event marker 515H, etc.). In one embodiment, these output indicators of pacing amplitudes are also displayed on a screen display of programmer 125. In a further embodiment, these output indicators of pacing amplitudes are also stored digitally in storage media associated with programmer 125.

By providing a recorded representation of electrograms, pacing event markers, and associated pacing amplitudes (or pulsewidths), the caregiver is more easily able to determine the particular pacing energy at which capture is lost. The energy at which capture is lost is determined by locating the particular event markers which are not followed by a substantially immediate cardiac depolarization associated with the particular chamber of the heart to which the pacing energy is being delivered. The strip chart conveniently provides a representation of the pacing energy (e.g., amplitude or pulsewidth) that is easily referred to each corresponding pace, in this case, by being printed directly below the event marker associated with that pace. This recorded representation of pacing energy makes it easy for the caregiver to determine proper pacing thresholds to be used to ensure adequate pacing, while minimizing energy drain to prolong the useful life of implanted device 105.

Figure 6:
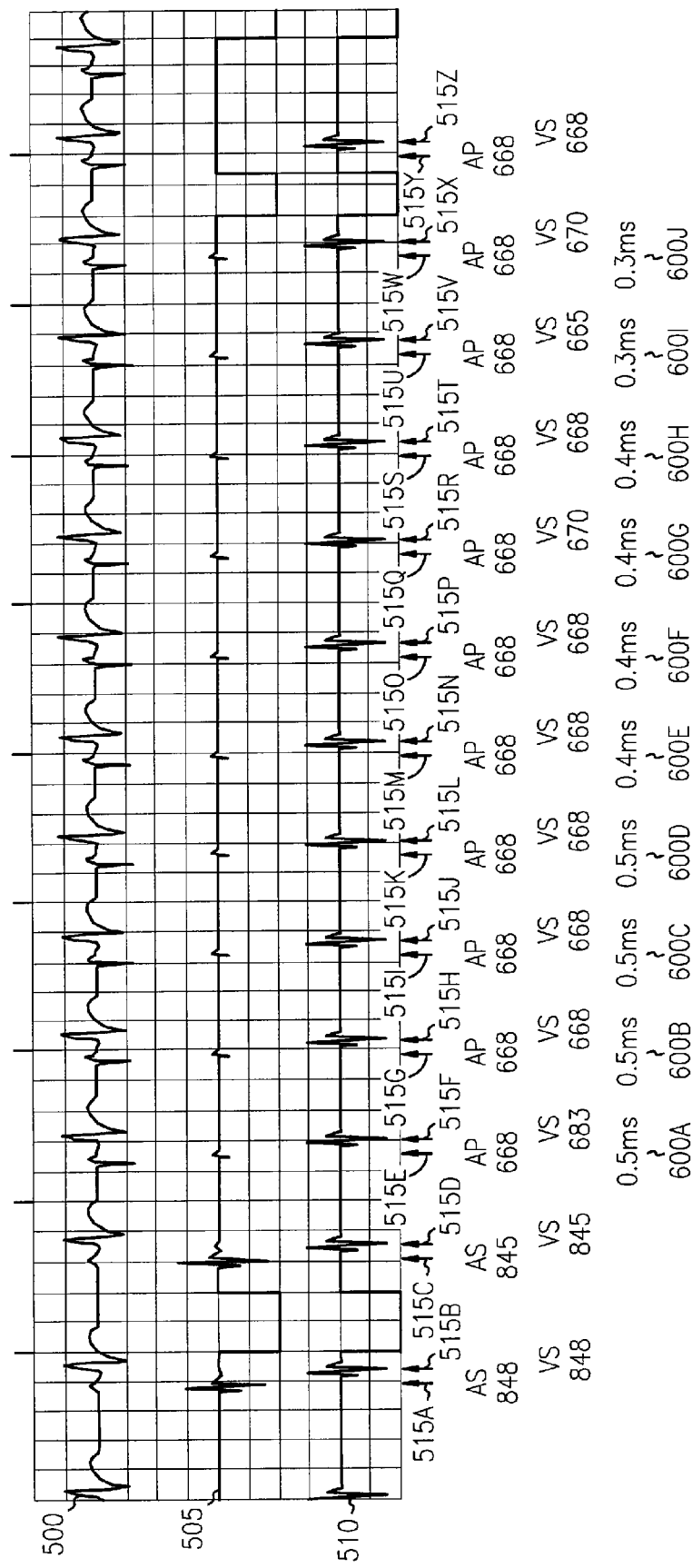
FIG. 6 is an example of a strip chart recording, similar to FIG. 5, in which the output indicators provide recorded indications of pacing pulsewidth, rather than amplitude, during pacing threshold testing.

FIG. 6 is an example of a strip chart recording, similar to FIG. 5, in which the output indicators 600A-J provide recorded indications of pacing pulsewidth for a pacing threshold test that varies pacing energy by varying pacing pulsewidth, rather than amplitude. In FIG. 6, because atrial pacing pulsewidth is being varied to determine atrial pacing thresholds, the output indicators of atrial pulsewidth are printed below their corresponding event markers (e.g., output indicator 600A of 0.5 milliseconds corresponds to atrial pace event marker 515E, output indicator 600B of 0.5 milliseconds corresponds to atrial pace event marker 515G, etc.).

In one embodiment, programmer 125 automatically selects the appropriate electrogram (e.g., atrial or ventricular) to be displayed on the screen display of programmer 125 during the threshold test, based on the particular chamber for which thresholds are being tested if that electrogram is not already being displayed on the screen display of programmer 125. In another embodiment, the screen display of electrogram corresponding to the chamber being tested for pacing thresholds automatically provides an enlarged view of that electrogram during the threshold test of that chamber. This makes it convenient for the caregiver to view small, not easily discernable evoked response artifacts. This makes it easy, for example, for the physician to see if a P-wave results from an atrial pace at a particular energy, otherwise the P-wave may be quite difficult to see.

CONCLUSION

This document describes, among other things, portions of a cardiac rhythm management system including a user interface for performing therapy energy threshold tests. In one embodiment, the user interface includes recorded indications of the energy corresponding to paced events, so that the caregiver can easily determine the point at which capture was lost. This recorded representation of pacing energy makes it easy for the caregiver to determine proper pacing thresholds to be used to ensure adequate pacing, while minimizing energy drain to prolong the useful life of the implanted device.

It is to be understood that the above description is intended to be illustrative, and not restrictive. Many other embodiments will be apparent to those of skill in the art upon reviewing the above description. For example, although aspects of the present system have been described with respect to threshold testing of pacing thresholds, it is understood that the user interface could provide similar useful operation during testing of defibrillation thresholds. In another example, the recorded output indicator of therapy energy need not be provided as a printed output; such recorded output can also be stored electronically, such as together with corresponding electrograms and event markers, for subsequent viewing on the screen display of the programmer or elsewhere. Other variations are also possible. The scope of the invention should, therefore, be determined with reference to the appended claims, along with the full scope of equivalents to which such claims are entitled.

What is claimed is:

1. A cardiac rhythm management system comprising:
    an external user interface, the user interface including:
        a communication module, adapted for wireless communicative coupling to an implantable device; and
        alphanumeric output indicators of pacing energy associated with each instance of pacing therapy delivery by the implantable device, wherein the indicators of pacing energy provides information about a pacing pulse voltage, wherein a plurality of the indicators are concurrently shown.

2. The cardiac rhythm management system of claim 1, in which the external user interface further includes at least one of:
    a display monitor displaying the indicator of pulse voltage in association with an indication of the instance of pacing therapy delivered by the implantable device;
    a strip chart printer recording the indicator of pulse voltage in association with an indication of the instance of pacing therapy delivered by the implantable device; and
    a memory circuit storing the indicator of pulse voltage in association with an indication of the instance of pacing therapy delivered by the implantable device.

3. The system of claim 1, in which the external user interface further includes at least one of:
    a therapy marker associated with an instance of therapy delivery by the implantable device; and
    a representation of a cardiac signal acquired by the implantable device.

4. The system of claim 3, in which at least one of the output indicator of pulse voltage and the therapy marker is associated with each instance of pacing therapy delivered by the implantable device.

5. The system of claim 4, further including a printer adapted to print at least one of the output indicator of pulse voltage, the therapy marker, and the representation of the cardiac signal.

6. The system of claim 4, further including a user interface screen adapted to display at least one of the output indicator of pulse voltage, the therapy marker, and the representation of the cardiac signal.

7. A cardiac rhythm management system comprising:
    an external user interface, the user interface including:
        a communication module, adapted for wireless communicative coupling to an implantable device; and
        alphanumeric output indicators of pacing energy associated with each instance of pacing therapy delivery by the implantable device, wherein the indicators of pacing energy provides information about a pacing pulsewidth, wherein a plurality of the indicators are concurrently shown.

8. The cardiac rhythm management system of claim 7, in which the external user interface further includes at least one of:
    a display monitor displaying the indicator of the pulsewidth in association with an indication of the instance of pacing therapy delivered by the implantable device;
    a strip chart printer recording the indicator of the pulsewidth in association with an indication of the instance of pacing therapy delivered by the implantable device; and
    a memory circuit storing the indicator of the pulsewidth in association with an indication of the instance of pacing therapy delivered by the implantable device.

9. The system of claim 7, in which the external user interface further includes at least one of:
    a therapy marker associated with an instance of therapy delivery by the implantable device; and
    a representation of a cardiac signal acquired by the implantable device.

10. The system of claim 9, in which at least one of the output indicator of the pulsewidth and the therapy marker is associated with each instance of pacing therapy delivered by the implantable device.

11. The system of claim 10, further including a printer adapted to print at least one of the output indicator of the pulsewidth, the therapy marker, and the representation of the cardiac signal.

12. The system of claim 10, further including a user interface screen adapted to display at least one of the output indicator of the pulsewidth, the therapy marker, and the representation of the cardiac signal.

13. A cardiac rhythm management system comprising:
    an external user interface, the user interface including:
        a communication module, adapted for wireless communicative coupling to an implantable device; and
        alphanumeric output indicators of pacing energy associated with each instance of pacing therapy delivery by the implantable device, wherein the indicators of pacing energy provides information about a pacing voltage amplitude and a pacing pulsewidth, wherein a plurality of the indicators are concurrently shown.

14. The cardiac rhythm management system of claim 13, in which the external user interface further includes at least one of:
    a display monitor displaying the indicator of the voltage amplitude and the pulsewidth in association with an indication of the instance of pacing therapy delivered by the implantable device;
    a strip chart printer recording the indicator of the voltage amplitude and the pulsewidth in association with an indication of the instance of pacing therapy delivered by the implantable device; and
    a memory circuit storing the indicator of the voltage amplitude and the pulsewidth in association with an indication of the instance of pacing therapy delivered by the implantable device.

15. The system of claim 13, in which the external user interface further includes at least one of:
    a therapy marker associated with an instance of therapy delivery by the implantable device; and a representation of a cardiac signal acquired by the implantable device.

16. The system of claim 15, in which at least one of the output indicator of the voltage amplitude and the pulsewidth and the therapy marker is associated with each instance of pacing therapy delivered by the implantable device.

17. The system of claim 16, further including a printer adapted to print at least one of the output indicator of the voltage amplitude and the pulsewidth, the therapy marker, and the representation of the cardiac signal.

18. The system of claim 16, further including a user interface screen adapted to display at least one of the output indicator of the voltage amplitude and the pulsewidth, the therapy marker, and the representation of the cardiac signal.

19. A cardiac rhythm management system comprising:
  an external user interface, the user interface including:
    a communication module, adapted for wireless communicative coupling to an implantable device; and
    alphanumeric output indicators of pacing energy associated with each instance of pacing therapy delivery by the implantable device, wherein the indicators of pacing energy provides information about a pacing current, wherein a plurality of the indicators are concurrently shown.

20. A cardiac rhythm management system comprising:
  an external user interface, the user interface including:
    a communication module, adapted for wireless communicative coupling to an implantable device; and
    alphanumeric output indicators of pacing energy associated with each instance of pacing therapy delivery by the implantable device, wherein the indicators of pacing energy provides information about a pacing energy, wherein a plurality of the indicators are concurrently shown.

* * * * *